United States Patent [19]

Brogli et al.

[11] Patent Number: 5,177,247
[45] Date of Patent: Jan. 5, 1993

[54] PROCESS FOR THE PREPARATION OF HYDROXYPHENYLPROPIONATES

[75] Inventors: Franz Brogli, Hofstetten; Guido Kälin, Füllinsdorf, both of Switzerland

[73] Assignee: Ciba-Geigy Corporation, Ardsley, N.Y.

[21] Appl. No.: 675,358

[22] Filed: Mar. 22, 1991

[30] Foreign Application Priority Data

Mar. 30, 1990 [CH] Switzerland .......... 1057/90

[51] Int. Cl.$^5$ .............................. C07C 69/76
[52] U.S. Cl. ........................................ 560/75
[58] Field of Search .......................... 560/75

[56] References Cited

U.S. PATENT DOCUMENTS

| | | | |
|---|---|---|---|
| 3,984,460 | 10/1976 | Spivack | 260/473 F |
| 4,049,713 | 9/1977 | Spivack | 260/559 R |
| 4,093,587 | 6/1978 | Spivack | 260/45.8 |
| 4,101,550 | 7/1978 | Spivack | 544/387 |

*Primary Examiner*—Paul J. Killos
*Attorney, Agent, or Firm*—Luther A. R. Hall

[57] ABSTRACT

Hydroxyphenylpropionates of formula

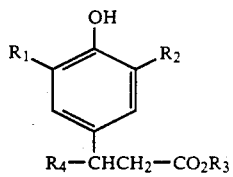

wherein $R_1$ to $R_4$ are as defined in claim 1, are prepared by reacting the appropriate phenol and acrylate components in the presence of the sodium and potassium salt of said phenol component.

6 Claims, No Drawings

PROCESS FOR THE PREPARATION OF HYDROXYPHENYLPROPIONATES

The present invention relates to a process for the preparation of hydroxyphenylpropionates.

Hydroxyphenylpropionates are normally prepared by the "Michael addition " of a phenol and an alkyl acrylate in the presence of a basic catalyst, as disclosed, for example, in DE-A 3 390 557. The adducts, viz. hydroxyphenylpropionates, can then be freed from by-products by crystallisation or, as described in U.S. Pat. No. 3,330,859 and U.S. Pat. No. 3,354,250, by distillation.

The hydroxyphenylpropionates so obtained are important intermediates for the preparation of antioxidants for synthetic polymers, especially for the polyolefins described in the above publications. By altering the molecular weight of the ester group it is possible to meet specific requirements which are made of an antioxidant, for example low volatility. This alteration can be effected directly by the synthesis or also indirectly, for example by transesterifying an already prepared hydroxyphenylpropionate.

It is now been found that the above Michael addition proceeds markedly better by carrying out the reaction of phenol and alkyl acrylate in the presence of a mixture of a sodium phenolate and a potassium phenolate.

Accordingly, the invention relates to a process for the preparation of compounds of formula

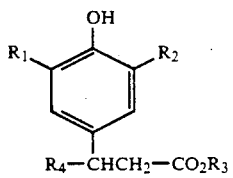

by reacting compounds of formula $$R_4-CH=CH-CO_2R_3 \quad (2)$$

with compounds of formula

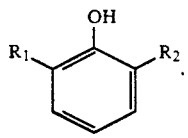

wherein $R_1$ to $R_3$ are each independently of the other alkyl of 1 to 4 carbon atoms, and $R_4$ is hydrogen or alkyl of 1 to 4 carbon atoms, in the presence of a base, and isolating the compounds of formula (1), which process comprises carrying out the reaction of a compound of formula (2) with a compound of formula (3) in the presence of a mixture of the compounds of formulae

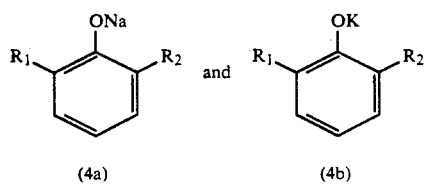

wherein $R_1$ and $R_2$ have the given meanings.

In the compounds of formals (1), the substituents $R_1$, $R_2$ and $R_3$ are each independently of one another alkyl of 1 to 4 carbon atoms, typically methyl, ethyl, propyl, butyl and tert-butyl. $R_4$ can have the meanings of $R_1$, $R_2$ and $R_3$ and may also additionally be hydrogen.

In the process of this invention, the bases employed are mixtures of the compounds of formulae (4a) and 4b). These bases are obtained by reacting the appropriate phenols of formula (3) with those bases which a re able to convert phenols into phenolates. Mention may be made in this connection, for example, of sodium and potassium methanolate, sodium and potassium tert-butylate and sodium and potassium amide and, more particularly, sodium and potassium hydroxide. Attention is drawn to the fact that, in the process of this invention, the eligible bases may additionally contain traces of these strong bases. The sodium and potassium salts of the compounds of formula (1) and of the starting compound of formula (3) are also bases whose presence facilitates the reaction.

The preparation of the mixture of bases usually comprises fusing a compound of formula (3) in a stirred reactor, in an inert gas atmosphere, and adding to the melt a molar excess of base in the form of an aqueous solution of, for example, sodium and potassium hydroxide. Water is then removed from the reaction mixture under reduced pressure to give a virtually non-aqueous suspension of the base in the phenol of formula (3).

The reaction of this suspension with the alkyl acrylate of formula (3) can subsequently be carried out in the same stirred reactor. As required, portion of the suspension may be added as catalyst to another batch for the preparation of the compounds of formula (1).

The molar ratio of the compound of formula (4a) to the compound of formula (4b) in the reaction mixture is preferably 0.05:1 to 20:1. The molar ratio of the compounds of formulae (4a) and (4b) to the phenol of formula (3) is conveniently 0.001 to 0.15. The alkyl acrylate of formula (2 ) is preferably used in a molar excess of up to 100%, based on the compound of formula (3). A temperature range of 90° to 150° C. has been found particularly suitable for carrying out the reaction. The pressure in the reactor is preferably 0 to 4 bar.

The process of this invention is particularly suitable for preparing a compound of formula (1), wherein $R_1$ and $R_2$ are tert-butyl, $R_3$ is methyl and $R_4$ is hydrogen. The process is carried out using a 5 to 40% molar excess of methyl acrylate, based on the phenol of formula (3), in the temperature range form 100° to 120° C. and under a pressure of 0 to 2 bar. The compounds of formulae (4a) and (4b) are present in the mixture of bases comprising said compounds in the molar ratios of 1:0.2 to 1:10 (compound of formula (4a) to compound of formula (4b)). The molar ratio of base (compounds of formulae (4a) and (4b)) to phenol of formula (3) is 0.005 to 0.1.

The compounds of formula (1) can be isolated in a manner known per se, for example by crystallisation or distillation under reduced pressure or by rectification, as described in Swiss patent application No. 1058/90-0.

In a preferred embodiment of the process, the base is precipitated with a carboxylic acid, preferably with formic or acetic acid, after the reaction and before the isolation of the compound of formula (1), and the salt is collected by filtration, also as described in Swiss patent application No. 1058/90-0.

The substantial shortening of the reaction time of the Michael addition carried out in the process of this invention results in markedly shorter sojourn times in the reactor and hence in lower periodic costs, especially when the reaction is carried out on an industrial scale.

The invention is illustrated by the following non-limitative Example in which, unless otherwise stated, percentage are by weight. The same applies to the remainder of the description and the claims.

EXAMPLE

A 2 liter jacketed flask with anchor stirrer is charged at 40° C. with 600 g of fused 2,6-di-tert-butylphenol. After blanketing with nitrogen, the contents of the flask are heated to 100° C. Then 6.5 g of aqueous potassium hydroxide (50%) and 2.3 g of aqueous sodium hydroxide (50%) are added to the reaction mixture and water is removed at 100° C. over 1 hour under a pressure of 20 mbar. The pressure is then reduced with nitrogen. Subsequently 325 g of methyl acrylate are added dropwise over 2 hours at 115° C. and the reaction is allowed to continue until a clear solution forms. The pressure in the reactor is slowly reduced to 10 mbar and excess methyl acrylate is removed at a final temperature of 115° C. After reducing the pressure with nitrogen, the base is neutralised with 9.8 g of formic acid (100%) and the precipitate is isolated by filtration. The yield of methyl 3,5-di-tert-butyl-4-hydroxyphenyl-1-propionate is found to be 93.6% by liquid chromatography after a total reaction time of 2.5 hours in the reaction mass.

What is claimed is:

1. An improved process for the preparation of a compound of formula

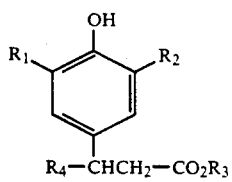

by reacting a compound of formula $$R_4-CH=CH-CO_2R_3 \qquad (2)$$

with a compound of formula

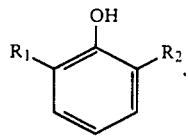

wherein $R_1$ to $R_3$ are each independently of the other alkyl of 1 to 4 carbon atoms, and $R_4$ is hydrogen or alkyl of 1 to 4 carbon atoms, in the presence of a base, and isolating said compound of formula (1), wherein the improvement comprises carrying out the reaction of a compound of formula (2) with a compound of formula (3) in the presence of a mixture of the compounds of formulae

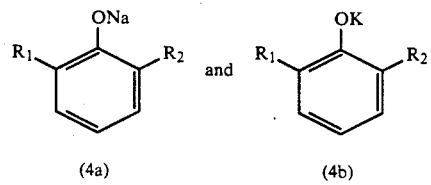

wherein $R_1$ and $R_2$ have the given meanings.

2. A process according to claim 1, wherein the molar ration of the compound of formula (4a) to the compound of formula (4b) is 0.05:1 to 20:1.

3. A process according to claim 1, wherein the molar ratio of the compounds of formulae (4a) and (4b) to the compound of formula (3) is 0.001 to 0.15.

4. A process according to claim 1, wherein a molar excess of up to 100% of the compound of formula (2) is used, based on the compound of formula (3).

5. A process according to claim 1, wherein the reaction of the compound of formula (2) with the compound of formula (3) is carried out in the temperature range from 90° to 150° C. and under a pressure of 0 to 4 bar.

6. A process according to any one of claims 1 to 5 for the preparation of a compound of formula (1), wherein $R_1$ and $R_2$ are tert-butyl, $R_3$ is methyl and $R_4$ is hydrogen, which process comprises carrying out the reaction in the temperature range from 100° to 120° C. and under a pressure of 0 to 2 bar, using a 5 to 40% molar excess of compound of formula (2), based on the compound of formula (3), wherein $R_1$ and $R_4$ have the given meanings, in the presence of a mixture of the compounds of formulae (4a) and (4b), wherein $R_1$ and $R_2$ have the given meanings, using the compounds of formulae (4a) and (4b) in the molar ratio of 1:0.2 to 1:10, and the molar ration of the compounds of formulae (4a) and (4b) to the compound of formula (3) being 0.005 to 0.1.

* * * * *